US 7,087,053 B2

(12) United States Patent
Vanney

(10) Patent No.: US 7,087,053 B2
(45) Date of Patent: Aug. 8, 2006

(54) CATHETER WITH BIFURCATED, COLLAPSIBLE TIP FOR SENSING AND ABLATING

(75) Inventor: Guy P. Vanney, Blaine, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 236 days.

(21) Appl. No.: 10/857,423

(22) Filed: May 27, 2004

(65) Prior Publication Data

US 2005/0267463 A1    Dec. 1, 2005

(51) Int. Cl.
*A61B 18/18* (2006.01)
(52) U.S. Cl. .......................................... 606/41; 606/47
(58) Field of Classification Search ................. 606/41
See application file for complete search history.

(56) References Cited

U.S. PATENT DOCUMENTS

| | | |
|---|---|---|
| 5,334,193 A | 8/1994 | Nardella |
| 5,536,267 A * | 7/1996 | Edwards et al. ............... 606/41 |
| 5,542,945 A * | 8/1996 | Fritzsch ....................... 606/48 |
| 5,555,883 A | 9/1996 | Avitall |
| 5,702,438 A | 12/1997 | Avitall |
| 5,730,704 A | 3/1998 | Avitall |
| 5,776,111 A | 7/1998 | Tesio |
| 5,860,974 A | 1/1999 | Abele |
| 5,871,483 A | 2/1999 | Jackson et al. |
| 5,885,278 A | 3/1999 | Fleischmann |
| 5,891,138 A | 4/1999 | Tu et al. |
| 5,916,213 A | 6/1999 | Haissaguerre |
| 6,068,629 A | 5/2000 | Haissaguerre |
| 6,071,274 A | 6/2000 | Thompson |
| 6,071,279 A | 6/2000 | Whayne |
| 6,071,280 A | 6/2000 | Edwards et al. |
| 6,071,282 A | 6/2000 | Fleischman |
| 6,076,012 A | 6/2000 | Swanson |
| 6,099,526 A | 8/2000 | Whayne et al. |
| 6,129,685 A | 10/2000 | Howard, III |
| 6,142,993 A | 11/2000 | Whayne et al. |
| 6,190,349 B1 | 2/2001 | Ash |
| 6,214,002 B1 | 4/2001 | Fleischman |
| 6,238,393 B1 | 5/2001 | Mulier et al. |
| 6,241,724 B1 | 6/2001 | Fleischman et al. |
| 6,241,726 B1 | 6/2001 | Chia et al. |
| 6,241,754 B1 | 6/2001 | Swanson |
| 6,251,109 B1 | 6/2001 | Hassett et al. |
| 6,308,091 B1 | 10/2001 | Avitall |
| 6,314,962 B1 | 11/2001 | Vaska et al. |

(Continued)

FOREIGN PATENT DOCUMENTS

WO         WO95/10319         4/1995

*Primary Examiner*—Linda C. M. Dvorak
*Assistant Examiner*—Alex Toy
(74) *Attorney, Agent, or Firm*—Heimbecher & Assoc., LLC

(57) ABSTRACT

A sensing and ablation electrode includes bifurcated sensing limbs separated by an ablation web. The electrode is disposed on the distal end of a catheter. The sensing limbs each support an array of sensors that are individually wired for mapping and post ablation efficacy testing. The web includes a pair of pliable membranes that define a lumen and are adapted to collapse the cross-section of the electrode. One membrane defines a plurality of apertures for dispersing a conductive fluid medium as a virtual electrode. The sensors and the apertures all lie within substantially the same plane.

27 Claims, 11 Drawing Sheets

U.S. PATENT DOCUMENTS

| | | |
|---|---|---|
| 6,314,963 B1 | 11/2001 | Vaska et al. |
| 6,325,797 B1 | 12/2001 | Stewart et al. |
| 6,375,654 B1 | 4/2002 | McIntyre |
| 6,402,746 B1 | 6/2002 | Whayne et al. |
| 6,454,758 B1 | 9/2002 | Thompson et al. |
| 6,574,492 B1 | 6/2003 | Ben-Haim et al. |
| 2002/0002372 A1 | 1/2002 | Jahns et al. |
| 2002/0068934 A1 | 6/2002 | Edwards et al. |

* cited by examiner

CATHETER WITH BIFURCATED, COLLAPSIBLE TIP FOR SENSING AND ABLATING

BACKGROUND OF THE INVENTION a. Field of the Invention

This invention relates to catheters for diagnosing and treating tissue, particularly human cardiac tissue. In particular, the invention relates to an ablation catheter with a collapsible tip that contains a virtual electrode interposed between two sensor arrays at a distal portion of the catheter.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel near the surface of the body and is guided to a specific location within the body for examination, diagnosis, and treatment. For example, one procedure utilizes a catheter to convey an electrical stimulus to a selected location within the human body. Another procedure utilizes a catheter with sensing electrodes to monitor various forms of electrical activity in the human body.

Catheters are also used increasingly for medical procedures involving the human heart. Typically, the catheter is inserted in an artery or vein in the leg, neck, or arm of the patient and threaded, sometimes with the aid of a guide wire or introducer, through the vessels until a distal tip of the catheter reaches the desired location for the medical procedure in the heart.

A typical human heart includes a right ventricle, a right atrium, a left ventricle, and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle.

In the normal heart, contraction and relaxation of the heart muscle (myocardium) takes place in an organized fashion as electro-chemical signals pass sequentially through the myocardium from the sinoatrial (SA) node, which comprises a bundle of unique cells disposed in the wall of the right atrium, to the atrioventricular (AV) node and then along a well-defined route, which includes the His-Purkinje system, into the left and right ventricles. The AV node lies near the ostium of the coronary sinus in the interatrial septum in the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole, wherein the atria contract to empty and fill blood into the ventricles. The atrial depolarization from the SA node is detected by the AV node which, in turn, communicates the depolarization impulse into the ventricles via the bundle of His and Purkinje fibers following a brief conduction delay. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart, which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Other abnormal arrhythmias sometimes occur in the atria, which are referred to as atrial arrhythmia. Three of the most common atrial arrhythmia are ectopic atrial tachycardia, atrial fibrillation, and atrial flutter. Atrial fibrillation can result in significant patient discomfort and even death because of a number of associated problems, including the following: an irregular heart rate, which causes patient discomfort and anxiety; loss of synchronous atrioventricular contractions, which compromises cardiac hemodynamics, resulting in varying levels of congestive heart failure; and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems, and other difficulties.

An increasingly common medical procedure for the treatment of certain types of cardiac arrhythmia is catheter ablation. During conventional catheter ablation procedures, an energy source is placed in contact with cardiac tissue to heat the tissue and create a permanent scar or lesion that is electrically inactive or noncontractile. During one procedure, the lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). Ablation of fast or slow AV nodal pathways is disclosed in Singer, I., et al., "Catheter Ablation for Arrhythmias," Clinical Manual of Electrophysiology, pgs. 421–431 (1993).

Another medical procedure using ablation catheters with sheaths to ablate accessory pathways associated with W-P-W utilizing both a transseptal and retrograde approach is discussed in Saul, J. P., et al., "Catheter Ablation of Accessory Atrioventricular Pathways in Young Patients: Use of long vascular sheaths, the transseptal approach and a retrograde left posterior parallel approach," Journal of the American College of Cardiology, Vol. 21, no. 3, pgs. 571–583 (1 Mar. 1993). Other catheter ablation procedures are disclosed in Swartz, J. F., "Radiofrequency Endocardial Catheter Ablation of Accessory Atrioventricular Pathway Atrial Insertion Sites," Circulation, Vol. 87, no. 2, pgs. 487–499 (February 1993).

Ablation of a specific location within or near the heart requires the precise placement of the ablation catheter. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy (placement of the catheter in relation to known features of the heart, which are marked by radiopaque diagnostic catheters that are placed in or at known anatomical structures, such as the coronary sinus, high right atrium, and the right ventricle).

The energy necessary to ablate cardiac tissue and create a permanent lesion can be provided from a number of different sources. Originally, direct current was utilized although laser, microwave, ultrasound, and other forms of energy have also been utilized to perform ablation procedures. Because of problems associated with the use of direct current, however, radiofrequency (RF) has become the preferred source of energy for ablation procedures. The use of RF energy with an ablation catheter contained within a transseptal sheath for the treatment of W-P-W in the left atrium is disclosed in Swartz, J. F. et al., "Radiofrequency Endocardial Catheter Ablation of Accessory Atrioventricular Pathway Atrial Insertion Sites," Circulation, Vol. 87, pgs. 487–499 (1993). See also Tracey, C. N., "Radio Frequency Catheter Ablation of Ectopic Atrial Tachycardia Using Paced Activation Sequence Mapping," J. Am. Coll. Cardiol. Vol. 21, pgs. 910–917 (1993).

In addition to radiofrequency ablation catheters, thermal ablation catheters have been used. During thermal ablation procedures, a heating element, secured to the distal end of a catheter, heats thermally conductive fluid, which fluid then contacts the human tissue to raise its temperature for a sufficient period of time to ablate the tissue.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes.

To form linear lesions within the heart using a conventional ablation tip electrode requires the utilization of procedures such as a "drag burn." The term "linear lesion" as used herein means an elongate, continuous lesion, whether straight or curved, that blocks electrical conduction. During a "drag burn" procedure, while ablating energy is supplied to the tip electrode, the tip electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure, and other variables associated with a beating heart, especially an erratically beating heart. Unless an uninterrupted track of cardiac tissue is ablated, unablated tissue or incompletely ablated tissue may remain electrically active, permitting the continuation of the stray circuit that causes the arrhythmia.

It has been discovered that more efficient ablation may be achieved if a linear lesion of cardiac tissue is formed during a single ablation procedure. The ablation catheters commonly used to perform these ablation procedures produce electrically inactive or noncontractile tissue at a selected location by physical contact of the cardiac tissue with an electrode of the ablation catheter. Conventional tip electrodes with adjacent ring electrodes cannot perform this type of procedure, however, because of the high amount of energy that is necessary to ablate sufficient tissue to produce a complete linear lesion. Also, conventional ring electrode ablation may leave holes or gaps in a lesion, which can provide a pathway along which unwanted electrochemical signals can travel.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode, which often results in the formation of coagulum on the electrode, which reduces the efficiency of the ablation electrode. With direct contact between the electrode and the blood, some of the energy targeted for the tissue ablation is dissipated into the blood. To achieve efficient and effective ablation, coagulation of blood that is common with conventional ablation catheters should be avoided. This coagulation problem can be especially significant when linear ablation lesions or tracks are produced because such linear ablation procedures conventionally take more time than ablation procedures ablating only a single location.

As noted, before treatment by ablation, clinicians attempt to determine the actual path of travel of the stray electrical signals through cardiac tissue that cause the arrhythmia. Once an ablation procedure has been performed, it is necessary to determine whether the lesion formed is effective in circumventing the unwanted electrical pathways. At present this involves the alternate or concurrent use of sensing catheters. This means that either the ablation catheter is removed from the cardiac cavity and a sensing catheter is inserted in its place to measure the efficacy of the procedure, or additional sensing catheters are introduced simultaneously into the cardiac cavity. Both of these options are problematic. If the ablation catheter is removed and replaced with a sensing catheter, it is difficult to reposition the ablation catheter in the original position should additional energy need to be applied to increase the size or depth of the lesion to arrest the signals if the first ablation attempt was unsuccessful. In the alternate method, the introduction of additional sensing catheters simultaneously with the ablation catheter means that additional incisions must be made in the patient and additional vessels used to navigate the catheters into the heart. This increases the risk of the procedure to the patient and also causes greater patient discomfort.

In some instances, stray electrical signals find a pathway down the pulmonary veins and into the left atrium of the heart. In these instances, it may be advantageous to produce a circumferential lesion at or near the ostium of one or more of the pulmonary veins. Desirably, such a circumferential lesion would electrically isolate a pulmonary vein from the left atrium, completely blocking stray signals from traveling down the pulmonary vein and into the left atrium. It is desirable to have a catheter with a distal portion for forming such circumferential lesions in tissue while avoiding problems with existing designs.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

A sensing and ablation electrode includes bifurcated sensing limbs separated by an ablation web. The electrode is disposed on the distal end of a catheter. The sensing limbs each support an array of sensors that are individually wired for mapping and post ablation efficacy testing. The web includes a pair of pliable membranes that define a lumen and are adapted to collapse the cross-section of the electrode. One membrane defines a plurality of apertures for dispersing a conductive fluid medium as a virtual electrode. The sensors and the apertures all lie within substantially the same plane.

One embodiment of the invention is a cardiac sensing and ablation device for intravascular insertion in a patient. The cardiac sensing and ablation device is composed of a bifurcated sensing portion and an ablation portion. The bifurcated sensing portion is further composed of a first sensing limb, a first set of a plurality of sensors disposed upon the first sensing limb, a second sensing limb, parallel with but spaced apart from the first sensing limb, and a second set of a plurality of sensors disposed upon the second sensing limb. The ablation portion is disposed between the first sensing limb and the second sensing limb. The ablation portion is further composed of an electrode. The first set of sensors, the second set of sensors, and the electrode lie substantially within the same plane. The bifurcated sensing portion and the ablation portion may also assume a pre-shaped curved form. When assuming the curved form, the first set of sensors is positioned on a surface of the first sensing limb defining an outer surface of the curved form and the second set of sensors is positioned on a surface of the second sensing limb defining the outer surface of the curved form.

Another embodiment of the invention is a cardiac sensing and ablation system composed of a catheter and a sensing array and ablation electrode. The sensing array and ablation electrode is disposed on a distal end of the catheter. The sensing and ablation electrode is further is further composed of a first sensing limb with a first set of a plurality of sensors disposed upon the first sensing limb and a second sensing limb, parallel with but spaced apart from the first sensing limb with a second set of a plurality of sensors disposed upon the second sensing limb. A first membrane and a second membrane are additionally disposed between the first sensing limb and the second sensing limb. The first membrane defines a plurality of apertures adapted to disperse a fluid. The first set of sensors, the second set of sensors, and the plurality of apertures lie substantially within the same plane. An electrode lumen is defined between the first membrane, the second membrane, the first sensing limb, and the second sensing limb. An electrode conductor is positioned between the first membrane and the second membrane adjacent the plurality of apertures. The cardiac sensing and ablation system may further have a shape retention wire positioned within the sensing array and ablation electrode that assumes a curved form when not otherwise restrained and causes the sensing array and ablation electrode to assume a ribbon-like form following the curved form of the shape retention wire.

A further embodiment of the invention is a bifurcated, collapsible electrode for intravascular insertion in a patient. The electrode is composed of a first limb with a plurality of sensors disposed upon the first limb, a second limb, parallel with but spaced apart from the first limb, an electrode supported by the second sensing limb, and a flexible membrane connected with and disposed between the first limb and the second limb. The plurality of sensors and the electrode lie substantially within the same plane. The first limb and the second limb may assume a curved form. In this case, the plurality of sensors is positioned on a surface of the first limb and defines an outer surface of the curved form. A tissue contacting portion of the electrode is positioned on a surface of the second limb and also defines the outer surface of the curved form.

Other features, details, utilities, and advantages of the present invention will be apparent from the following more particular written description of various embodiments of the invention as further illustrated in the accompanying drawings and defined in the appended claims.

DETAILED DESCRIPTION OF THE INVENTION

The instant invention is directed to a unique sensing/ablation electrode provided on a distal portion of a catheter/introducer assembly. The sensing/ablation electrode is bifurcated providing two sets of sensor arrays separated by a virtual electrode for tissue ablation. The sensing/ablation electrode can be used for pre-treatment diagnostic sensing and for post ablation efficacy testing of a lesion formed by the ablation component without having to move the electrode or introduce additional catheters with sensor arrays into the patient.

Figure 1:
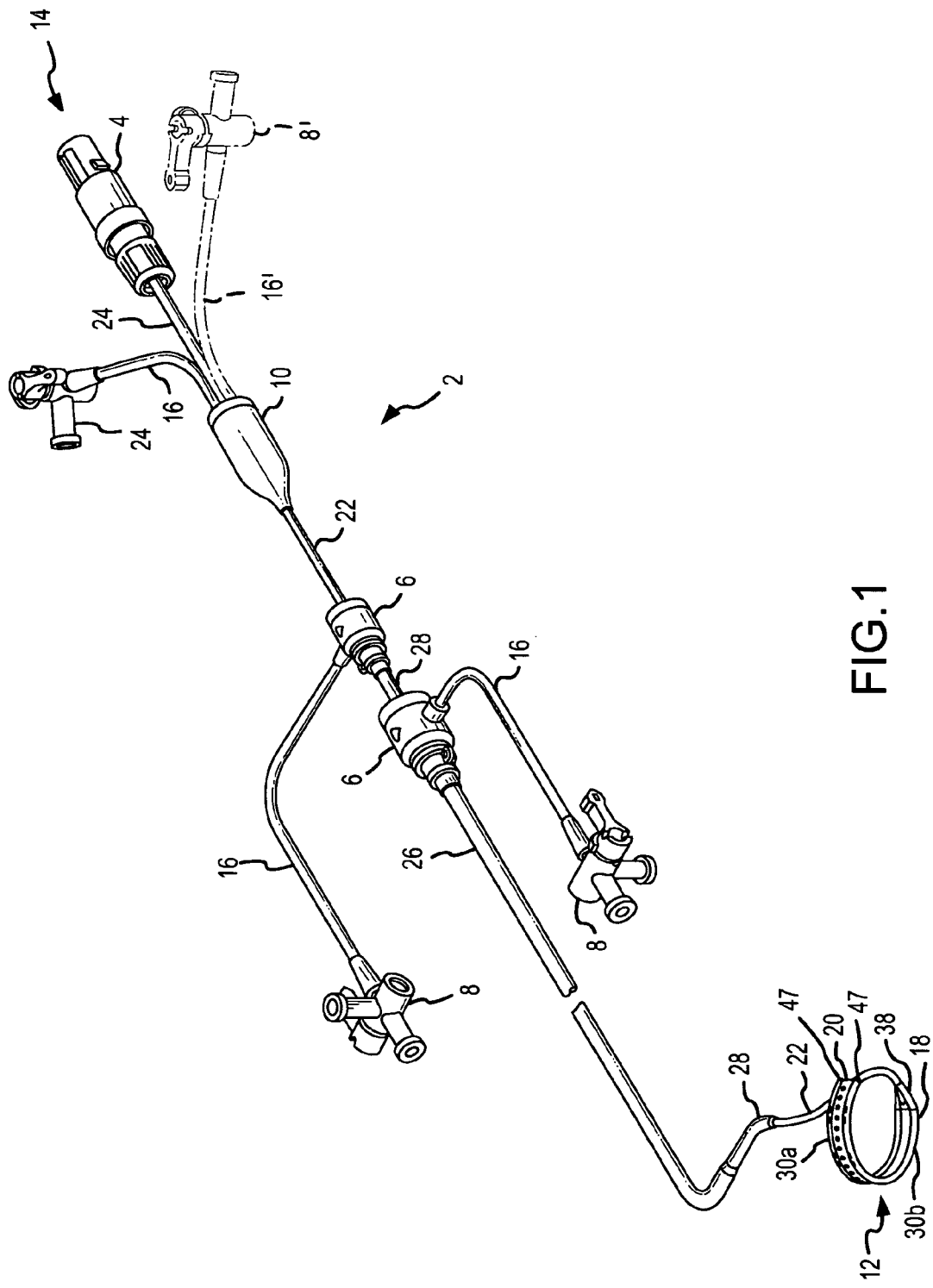
FIG. 1 is an isometric view of a catheter/introducer assembly including a sensing/ablation electrode according to one embodiment of the present invention.

FIG. 1 is an isometric view of a catheter/introducer assembly 2 according a first embodiment of the present invention. In this embodiment of the invention, a catheter 22 having a sensing/ablation electrode 18 at a distal end 12 and a handle interface 4 at a proximal end 14 is used in combination with an inner guiding introducer 28 and an outer guiding introducer 26 to facilitate formation of lesions on tissue, for example, cardiovascular tissue. The inner guiding introducer 28 is longer than and is inserted within the lumen of the outer guiding introducer 26. Alternatively, a single guiding introducer or a precurved transeptal sheath may be used instead of both the inner guiding introducer 28 and the outer guiding introducer 26. In general, introducers or precurved sheaths are shaped to facilitate placement of the sensing/ablation electrode 18 at the tissue surface to be ablated. As depicted in FIG. 1, for example, the outer guiding introducer 26 is formed with a curve at the distal end 12. Similarly, the inner guiding introducer 28 is formed with a curve at the distal end 12. Together, the curves in the guiding introducers 26, 28 help orient the catheter 22 as it emerges from the inner guiding introducer 26 in a cardiac cavity. Thus, the inner guiding introducer 28 and the outer guiding introducer 26 are used navigate a patient's vasculature to the heart and through its complex physiology to reach specific tissue to be ablated.

As shown in FIG. 1, each of the guiding introducers 26, 28 is connected with a hemostatic valve 6 at its proximal end to prevent blood or other fluid that fills the guiding introducers 26, 28 from leaking before the insertion of the catheter 22. The hemostatic valves 6 form tight seals around the shafts of the guiding introducers 26, 28 or the catheter 22 when inserted therein. Each hemostatic valve 6 may be have a port connected with a length of tubing 16 to a fluid introduction valve 8. The fluid introduction valves 8 may be connected with a fluid source, for example, saline or a drug, to easily introduce the fluid into the introducers, for example, to flush the introducer or to inject a drug in to the patient. Each of the fluid introduction valves 8 may control the flow of fluid into the hemostatic valves 16 and thereby the guiding introducers 26, 28.

The proximal end 14 of the catheter 22 may include a catheter boot 10 that seals around several components to allow the introduction of fluids and control mechanisms into the catheter 22. For example, at least one fluid introduction valve 8 with an attached length of tubing 16 may be coupled with the catheter boot 10. An optional fluid introduction valve 8' and correlative tube 16' (shown in phantom) may also be coupled with the catheter boot 10, for example, for the introduction of pressurized air in an embodiment incorporating a pneumatically controlled catheter or sensing/ablation tip (as further discussed below). A handle interface 4 for connection with a control handle, a generator, and/or sensing equipment (none shown) may be coupled with the catheter boot 10 via a control shaft 24. The control shaft 24 may enclose, for example, control wires for manipulating the catheter 22 or sensing/ablation electrode 18, conductors for energizing an electrode in the sensing/ablation electrode 18, and/or lead wires for connecting with sensors in the sensing/ablation electrode 18. The catheter boot 10 provides a sealed interface to shield the connections between such wires and fluid sources and one or more lumen in the catheter 22 through which they extend.

Figure 2:
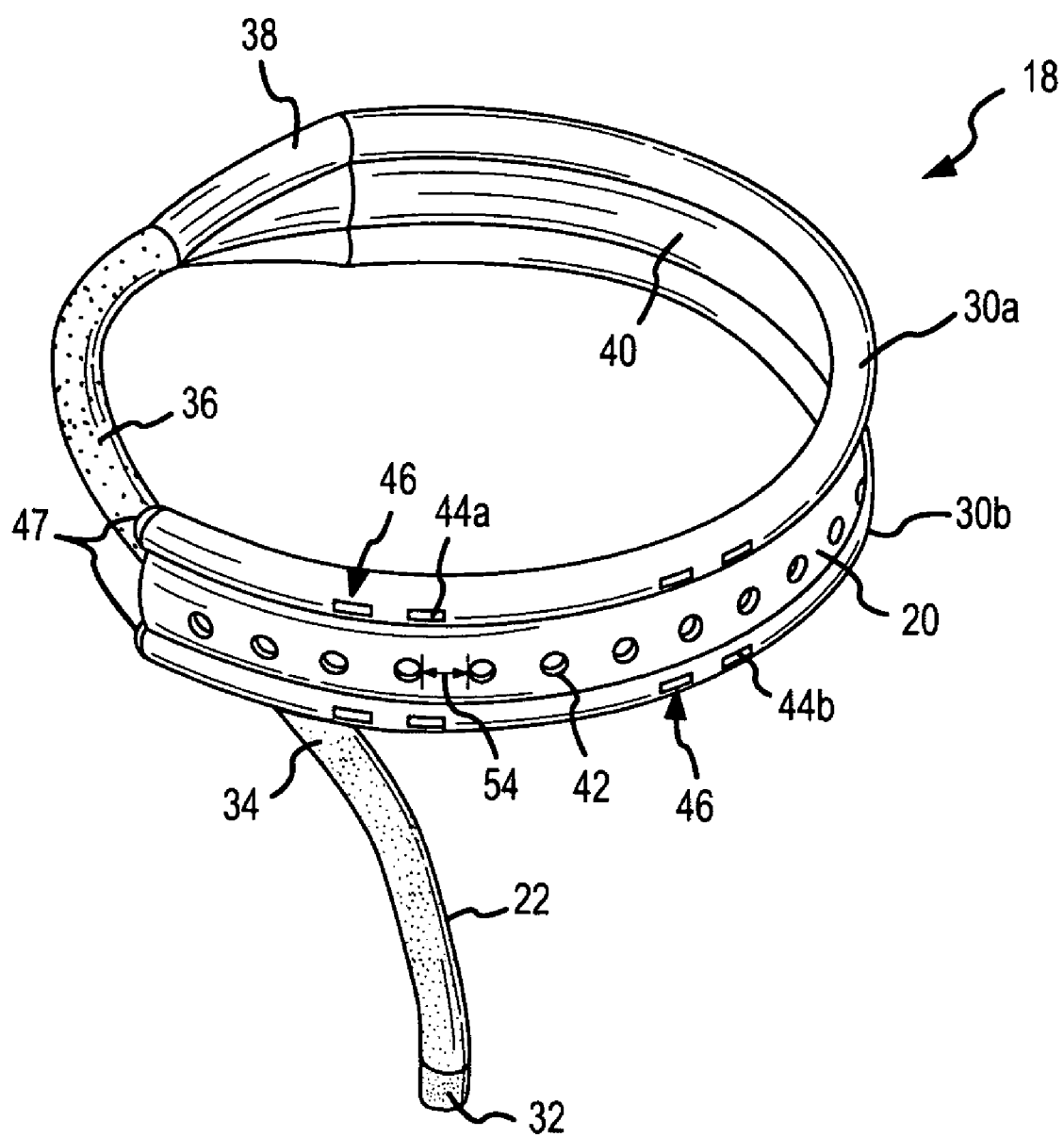
FIG. 2 is an isometric view of a distal portion of the catheter of FIG. 1 including the sensing/ablation electrode.

The distal end 12 of the catheter 22 including the sensing/ablation electrode 18 is shown in greater detail in FIG. 2. The catheter 22 consists mainly of a "straight" section 32 extending from the catheter boot 10 at the proximal end 14 to a point adjacent to the distal end 12 of the catheter/introducer assembly 2. At the distal end 12 the catheter 22 is composed of a first curved section 34 and a second curved section 36 before transitioning into the sensing/ablation electrode 18. The first curved section 34 is adjacent and distal to the straight section 32 and proximal and distal to the second curved section 36. The straight section 32, first curved section 34, and second curved section 36 together form a single, unitary structure of the catheter 22, but may be separate pieces joined together to form the catheter 22.

Each of the different sections of the catheter 22 may be constructed from a number of different polymers, for example, polypropylene, oriented polypropylene, polyethylene, polyethylene terephthalate, crystallized polyethylene terephthalate, polyester, polyvinyl chloride, and Pellethane®. Alternatively, the different sections of the catheter 22 may be composed, for example, of different formulations of Pebax® resins (AUTOFINA Chemicals, Inc. Philadelphia, Pa.), or other polyether-block co-polyamide polymers, which can be used to create desired materials stiffness within the different sections of the catheter 22. By using different formulations of the Pebax® resins, different mechanical properties (e.g., flexibility or stiffness) can be chosen for each of the sections along a catheter 22.

The catheter 22 may also be a braided catheter wherein the catheter wall includes a cylindrical braid of metal fibers, for example, stainless steel fibers. Such a metallic braid may be included in the catheter 22 to add stability to the catheter 22 and also to resist radial forces that might crush the catheter 22. Metallic braid also provides a framework to translate torsional forces imparted by the clinician on the proximal end 14 of the catheter 22 to the distal end 12 to rotate the catheter 22 for appropriate orientation of the sensing/ablation electrode 18.

The straight section 32 is generally the portion of the catheter 22 that remains within the vasculature of the patient while a sensing or ablation procedure is performed by a clinician. As shown in FIGS. 1 and 2, the sensing/ablation electrode 18 takes on a generally circular or C-shaped configuration when deployed from the inner guiding introducer 28. The first curved section 34 and second curved section 36 of the catheter 22 align the straight section 32 of the catheter 22 with respect to the sensing/ablation electrode 18. In particular, the distal end of the straight section 32 of a catheter 22 is oriented in a position where a longitudinal axis extending through the distal end of the straight section 32 passes orthogonally through the center of a circle defined by the C-shaped sensing/ablation electrode 18. In this manner the straight section 32 of the catheter 22 is spatially displaced from the sensing/ablation electrode 18 so that the straight section 32 is unlikely to interfere with the interface between the sensing/ablation electrode 18 and the cardiac tissue as further described below.

As depicted in FIG. 2, the sensing/ablation electrode 18 is connected to the second curved section 36 of the catheter 22 by a transition section 38. The sensing/ablation electrode 18 is composed of a distal sensing limb 30a and a proximal sensing limb 30b that are connected together on a first side by an ablation web 20 and on a second side by a backing web 40. The distal and proximal sensing limbs 30a, 30b extend from the transition section 38 in parallel planar curves to form the C-shape of the sensing/ablation electrode 18. Each of the distal and proximal sensing limbs 30a, 30b are generally circular in cross-section. The distal end of each of the distal and proximal sensing limbs 30a, 30b is sealed with a cap 47. The ablation web 20 spans the distance between the distal sensing limb 30a and the proximal sensing limb 30b and bows radially outward such that a line tangential to the surface of both the distal sensing limb 30a and the proximal sensing limb 30b on the side of the ablation web 20 is likewise tangential to a surface of the ablation web 20. The backing web 40 similarly spans the separation distance between the distal sensing limb 30a and the proximal sensing limb 30b and forms a surface contiguous with and opposite to the ablation web 20. The backing web 40 is also bowed to form a convex surface that extends inwardly toward the center of the circular area defined by the curvature of the sensing/ablation electrode 18.

Both the distal sensing limb 30a and the proximal sensing limb 30b define a series of apertures that form sensor windows 46 that expose corresponding distal sensors 44a on the distal sensing limb 30a and proximal sensors 44b on the proximal sensing limb 30b. The sensor windows 46 are dispersed linearly along the lengths of both the distal and proximal sensing limbs 30a, 30b. As indicated in FIGS. 2, 3A, 4A, and 5A, the sensing windows 46 may be arranged in pairs with greater spacing between each set of pairs of sensing windows 46 than the spacing between each sensing window 46 in each pair. It should be recognized that the sensing windows 46 may be otherwise arranged. For example, the sensor windows 46 may be grouped in different numbers, e.g., sets of three or four; may be grouped in uniform numbers, e.g., sets of two, three, and four; or they may be uniformly distributed along the length of the distal and proximal sensing limbs 30a, 30b.

The sensor windows 46, and correspondingly the distal and proximal sensors 44a, 44b are arranged on the distal and proximal sensing limbs 30a, 30b such that a line tangent to both the distal and proximal sensing limbs 30a, 30b would likewise interface with the sensor windows 46. It should be understood, however, that the sensor windows 46, and correspondingly the distal and proximal sensors 44a, 44b may be otherwise arranged about the surfaces of the distal and proximal sensing limbs 30a, 30b in order to effect the desired clinical result.

The ablation web 20 similarly defines a series of apertures that form dispersion ports 42. As depicted in FIG. 2, the dispersion ports 42 are oriented linearly and spaced equidistant from each other along the length of the ablation web 20. It should be apparent that the diversion ports 42 may not be so spaced or linearly arranged in other embodiments of the invention. The dispersion ports 42 in the present embodiment are spaced on the ablation web 20 equidistant between the proximal sensing limb 30b and the distal sensing limb 30a.

Figure 3A:
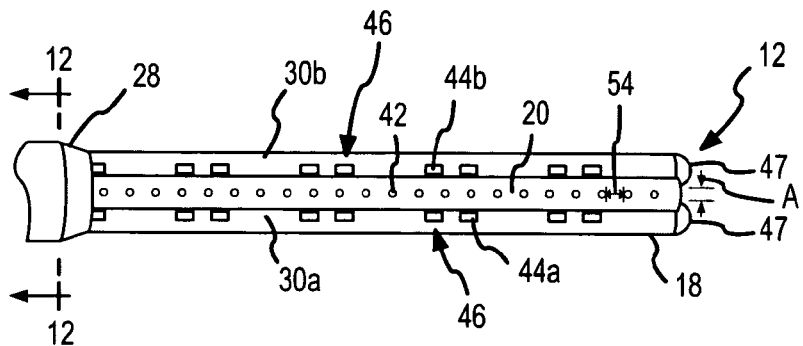
FIG. 3A is a schematic elevation view of the sensing/ablation electrode of FIG. 1 in an initial stage of deployment from the distal tip of the inner guiding introducer. For clarity, the sensing/ablation electrode is shown in a flat orientation, rather than the curved orientation of FIG. 2.

FIGS. 3A–5B depict the sensing/ablation electrode 18 on the distal end of the catheter 22 as it is deployed from within the inner guiding introducer 28 within a cardiac cavity. The sensing/ablation electrode 18 in each of FIGS. 3A–5B is depicted schematically as lying flat within a single plane rather than in the curved configuration of FIG. 2. This configuration is merely provided for ease of description as the sensing/ablation electrode 18 of the catheter 22 would actually form the curved shaped of FIG. 2 upon deployment from the inner guiding introducer 28. As is apparent from FIG. 2, the largest cross-sectional dimension of the deployed sensing/ablation electrode 18 is much larger than the diameter of the catheter 22. As shown in FIG. 3A, upon initial deployment of the sensing/ablation electrode 18, the separation distance A between the distal sensing limb 30a and the proximal sensing limb 30b is narrower than when the sensing/ablation electrode 18 is fully deployed. FIG. 4A shows the sensing/ablation electrode 18 at a second more advanced stage of deployment. As shown in FIG. 4A the separation A' between the distal sensing limb 30a and the proximal sensing limb 30b is greater than the separation distance A of the sensing/ablation electrode 18 in FIG. 3A. Finally when the sensing/ablation electrode 18 is fully deployed from the inner guiding introducer 28 as shown in FIG. 5A, the separation distance A" between the distal sensing limb 30a and the proximal sensing limb 30b is at its widest.

Figure 12:
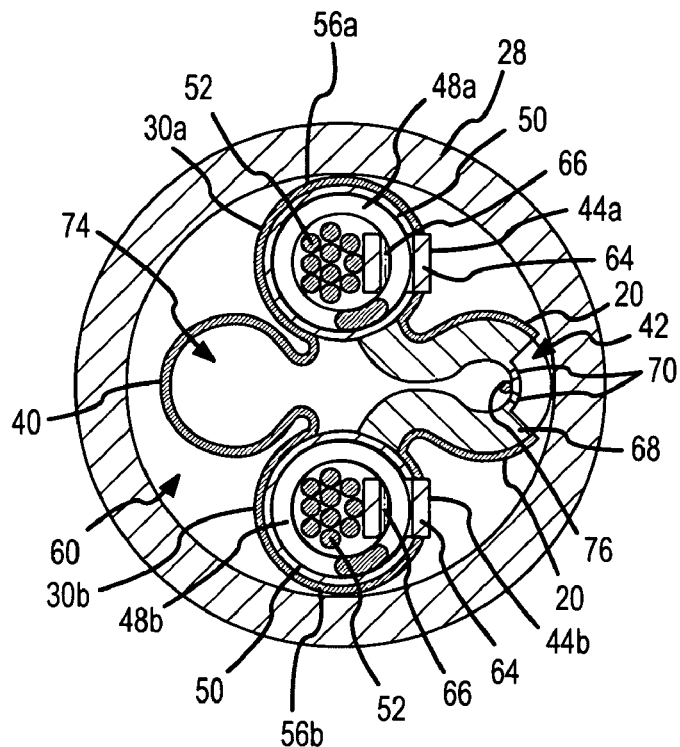
FIG. 12 is a cross-section view of the catheter within the inner guiding introducer taken along line 12—12 of FIG. 5A.

The separation distance between the distal sensing limb 30a and the proximal sensing 30b increases as the sensing/ablation electrode 18 is deployed from the inner guiding introducer 28 due to the collapsible design of the sensing/ablation electrode 18. As shown in FIG. 12, each of the ablation web 20 and the backing web 40 are flexible and bend near each of their interfaces with both the distal sensing limb 30a and the proximal sensing limb 30b. Each of the ablation web 20 and the backing web 40 also bows laterally outward from a plane bisecting each of the distal sensing limb 30a and proximal sensing limb 30b. When the separation distance between the distal sensing limb 30a and the proximal sensing 30b is at a minimum, each of the ablation web 20 and the backing web 40 bows further outward and defines an almost circular cross-sectional area as shown in FIG. 12. The ablation web 20 is backed an ablation membrane 68, described in greater detail below, which is similarly flexible and allows the ablation web 20 to bow radially outward as described.

Figure 4A:
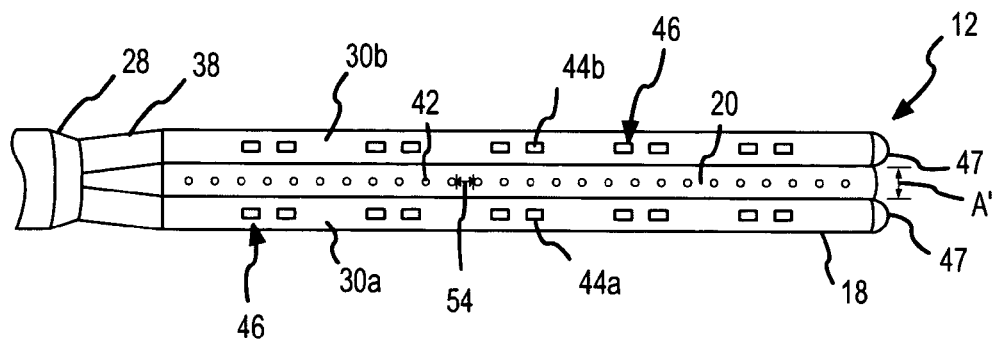
FIG. 4A is an elevation view of the sensing/ablation electrode of FIG. 1 in an intermediate stage of deployment from the distal tip of the inner guiding introducer. For clarity, the sensing/ablation electrode is shown in a flat orientation, rather than the curved orientation of FIG. 2.
Figure 5A:
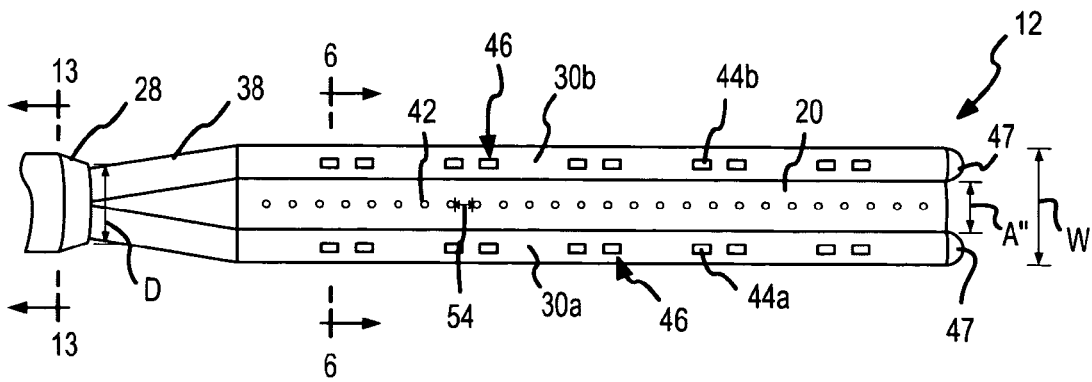
FIG. 5A is an elevation view of the sensing/ablation electrode of FIG. 1 fully deployed from the distal tip of the inner guiding introducer. For clarity, the sensing/ablation electrode is shown in a flat orientation, rather than the curved orientation of FIG. 2.
Figure 13:
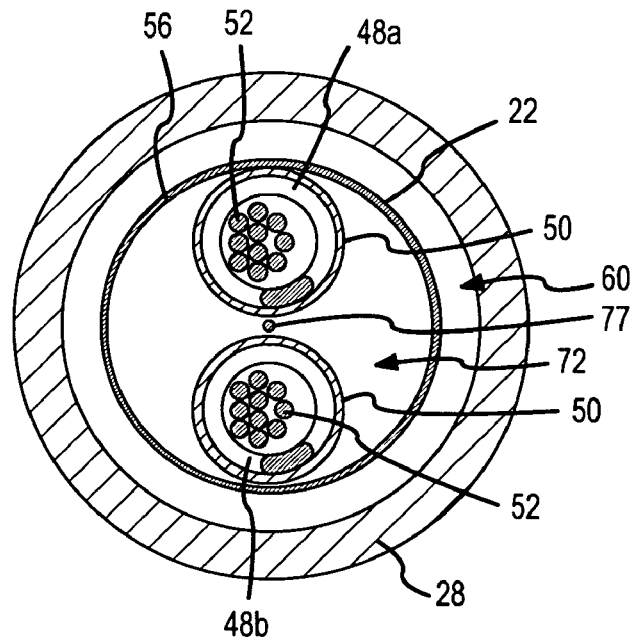
FIG. 13 is a cross-section view of the sensing/ablation electrode within the inner guiding introducer taken along line 13—13 of FIG. 3A.

The collapsible design of the sensing/ablation electrode 18 thereby allows the maximum cross-sectional width W of the sensing/ablation electrode 18 to be larger than the diameter D of the inner guiding introducer 28 when deployed. FIGS. 3A, 4A, and 5A can alternately be viewed as various stages of deployment or as various stages of retraction of the sensing/ablation catheter 18. As shown in FIGS. 4A and 5A, the ablation web 20 (and similarly the backing web 40, although not shown) converts to a transition web 62 in the region of the transition section 38, gradually decreasing in width as it progresses proximally. The transition section 38 reduces the separation distance between the distal sensing limb 30a and the proximal sensing limb 30b ultimately tapering the sensing/ablation electrode 18 to a width congruent with the diameter of the lumen 60 of the inner guiding introducer 28 (see FIG. 13). This tapering allows for the initial retraction of the sensing/ablation electrode 18 within the inner guiding introducer 28. The pliability and collapsibility of each of the transition web 62, the backing web 40, the ablation web 20, and the ablation membrane 68 as previously described allows for the full retraction of the sensing/ablation electrode 18 within the inner guiding introducer 28 (see FIG. 13).

Figure 3B:
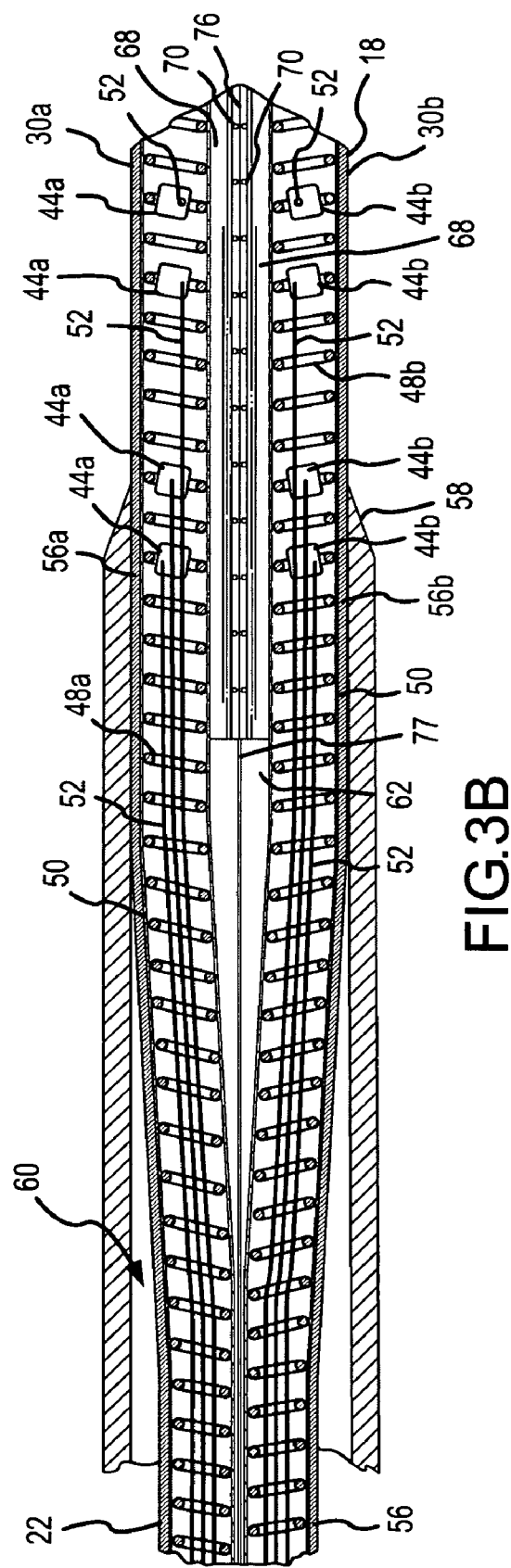
FIG. 3B is a cross-section view of the sensing/ablation electrode corresponding to FIG. 3A in an initial stage of deployment from the distal tip of the inner guiding introducer and further including a portion of the distal end of the catheter. The view of FIG. 3B corresponds to a cross-section of FIG. 3A parallel to the plane of the page and bisecting the catheter and introducer. The direction of the view is out of the page of FIG. 3A. The view just described has been further rotated 180° to orient the components of FIG. 3B in the same direction on the page as the components of FIG. 3A. For clarity, the sensing/ablation electrode is shown in a flat orientation, rather than the curved orientation of FIG. 2.
Figure 4B:
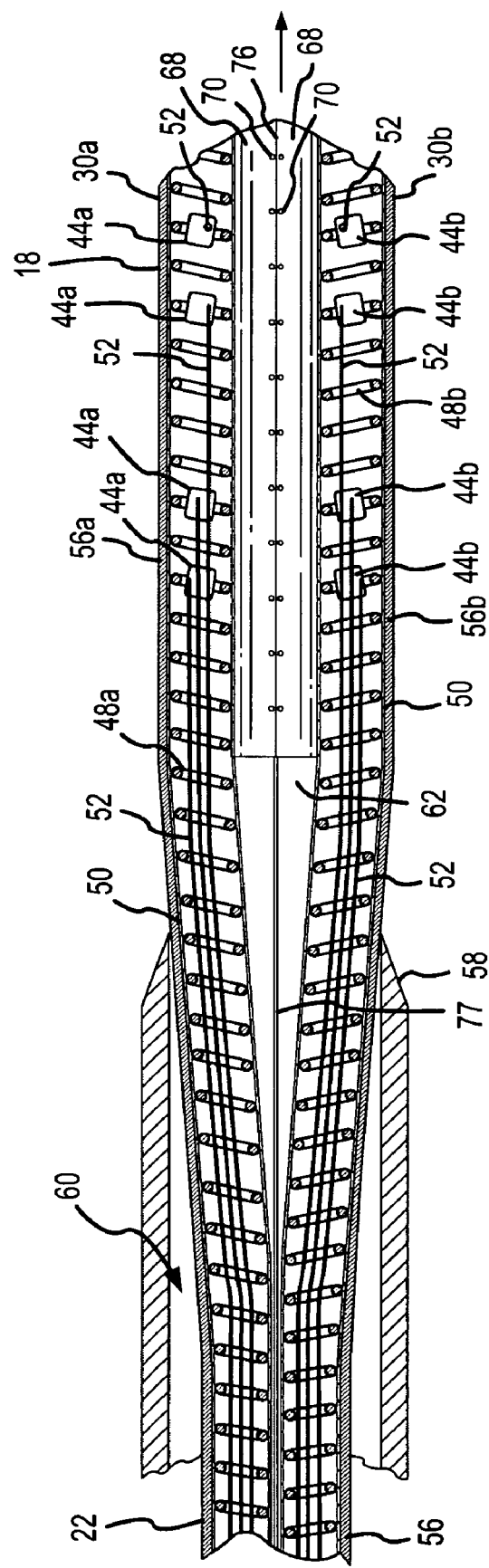
FIG. 4B is a cross-section view of the sensing/ablation electrode corresponding to FIG. 4A in an intermediate stage of deployment from the distal tip of the inner guiding introducer and further including a portion of the distal end of the catheter. The view of FIG. 4B corresponds to a cross-section of FIG. 4A parallel to the plane of the page and bisecting the catheter and introducer. The direction of the view is out of the page of FIG. 4A. The view just described has been further rotated 180° to orient the components of FIG. 4B in the same direction on the page as the components of FIG. 4A. For clarity, the sensing/ablation electrode is shown in a flat orientation, rather than the curved orientation of FIG. 2.
Figure 5B:
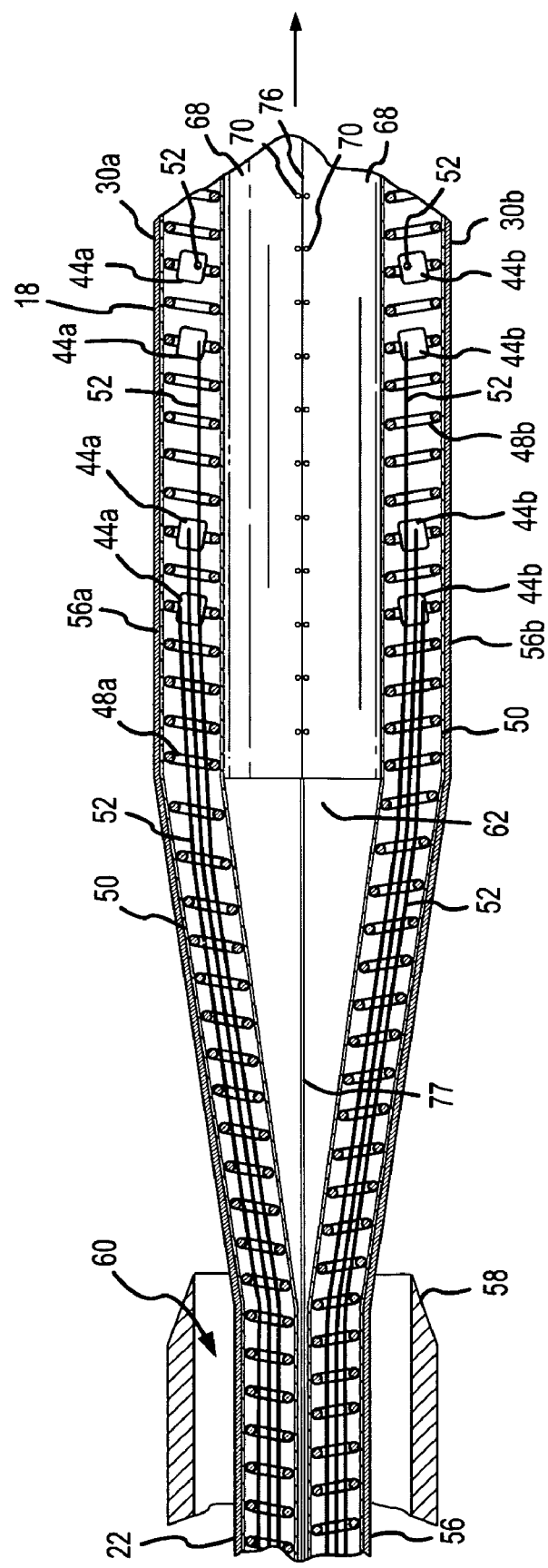
FIG. 5B is a cross-section view of the sensing/ablation electrode corresponding to FIG. 5A fully deployed from the distal tip of the inner guiding introducer and further including a portion of the distal end of the catheter. The view of FIG. 5B corresponds to a cross-section of FIG. 5A parallel to the plane of the page and bisecting the catheter and introducer. The direction of the view is out of the page of FIG. 5A. The view just described has been further rotated 180° to orient the components of FIG. 5B in the same direction on the page as the components of FIG. 5A. For clarity, the sensing/ablation electrode is shown in a flat orientation, rather than the curved orientation of FIG. 2.

FIGS. 3B, 4B, and 5B, are cross-sections of a portion of the sensing/ablation electrode 18 and the distal end 12 of the inner guiding introducer 28 corresponding generally to the various stages of deployment (or retraction) of the sensing/ablation electrode 18 of FIGS. 3A, 4A, and 5A respectively. The cross-sections of FIGS. 3B, 4B, and 5B are oriented from the perspective of a plane bisecting both the distal sensing limb 30a and the proximal sensing limb 30b with the direction of view orthogonal to the plane and coming out of the page depicted FIGS. 3A, 4A, and 5A. The view of the cross-sections just described are further rotated 180° in order that the distal end of the ablation/sensing electrode 18 is oriented in the same direction in FIGS. 3B, 4B, and 5B to correspond with the direction of the distal end of the ablation/sensing electrode 18 in FIGS. 3A, 4A, and 5A. Similar to FIG. 3A, therefore, the sensing/ablation electrode 18 in FIG. 3B is only partially deployed from the distal tip 58 of the inner guiding introducer 28.

As shown in FIG. 3B and similarly in FIG. 12, the tubular structure of the distal sensing limb 30a is provided by a distal coil 48a. Similarly, the proximal sensing limb 30b is supported by the structure of a proximal coil 48b. The distal and proximal coils 48a, 48b may be formed from helically-shaped wires. The distal and proximal coils 48a, 48b are each encased in a coil sleeve 50 to prevent entanglement between the windings of the distal coil 48a and the proximal coil 48b as they reside within the catheter 22 and the sensing/ablation electrode 18.

Figure 14:
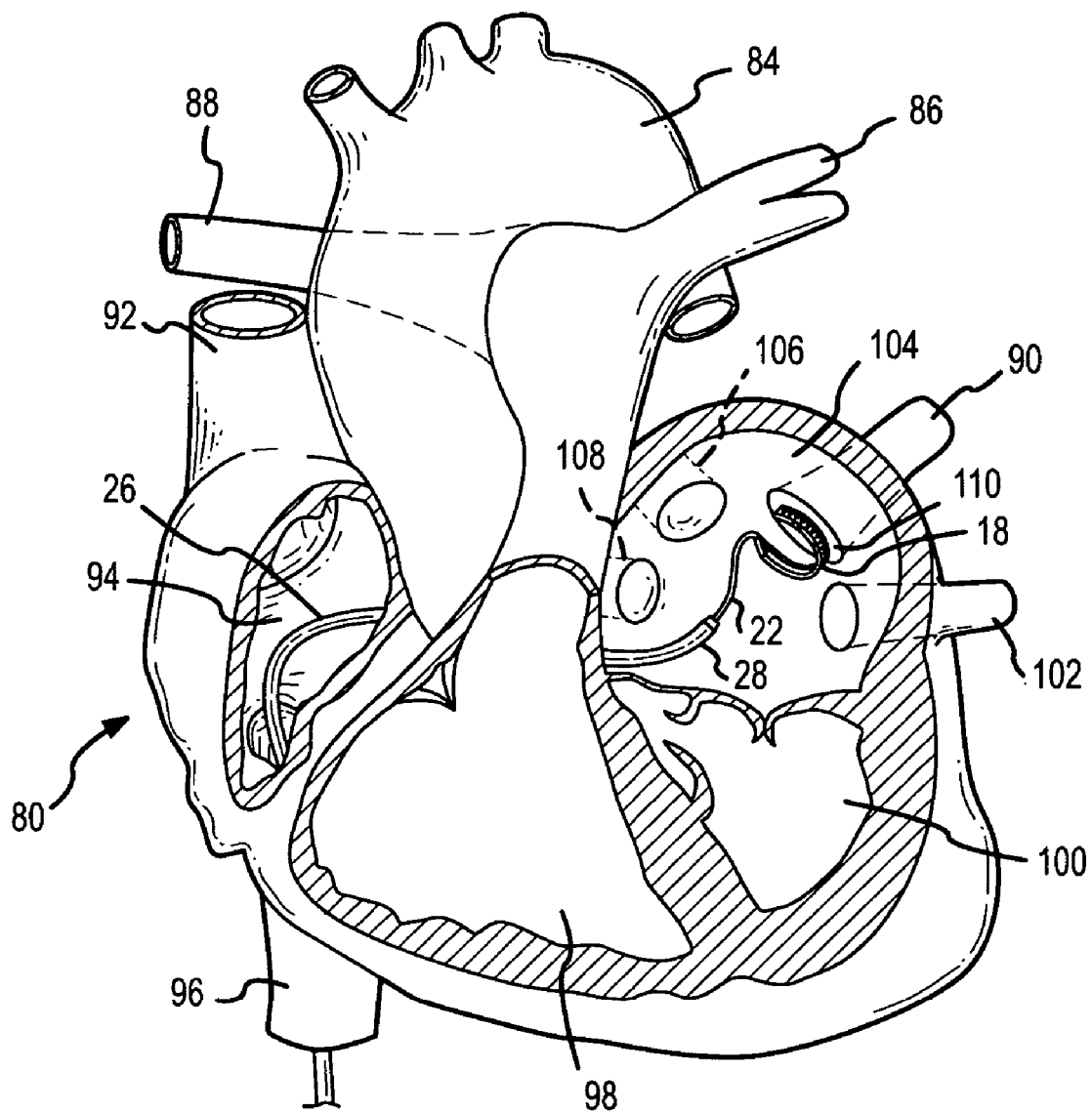
FIG. 14 is an isometric view of a heart with portions of the atria and ventricles broken away to reveal positioning of the sensing/ablation electrode depicted in, for example, FIGS. 1 and 2 in the left atrium, adjacent to the left superior pulmonary vein.
Figure 15:
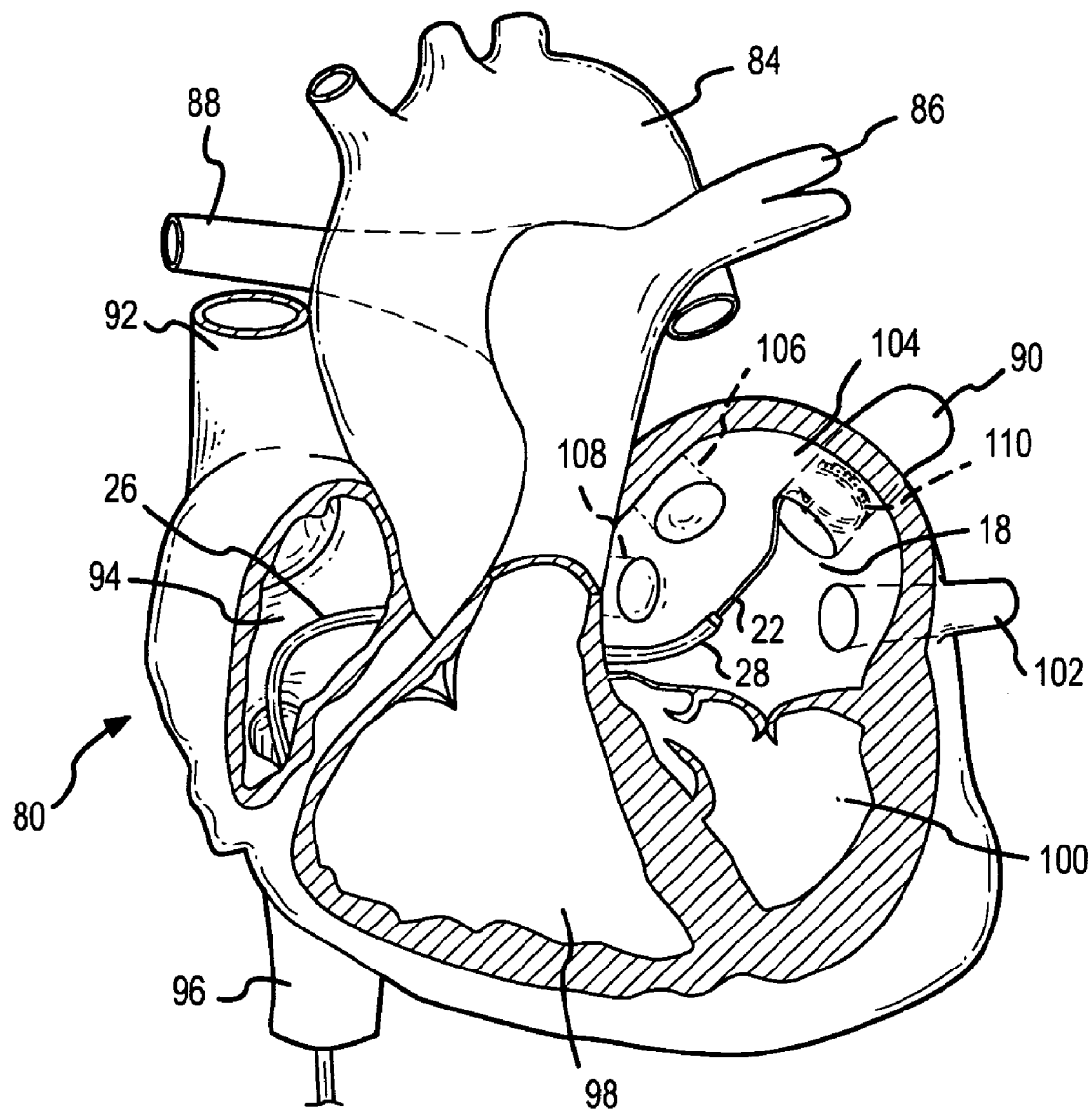
FIG. 15 is similar to FIG. 14, but depicts the sensing/ablation electrode positioned against tissue near the ostium of the left superior pulmonary vein.

In one embodiment, the distal and proximal coils 48a, 48b can be formed of a shape-retention or a shape-memory metal wire. The shape-retention or shape-memory wire is flexible while the clinician negotiates the catheter 22 through the vasculature to reach the heart and enter an atrial chamber. Once the distal end of the catheter 22 reaches the desired cardiac cavity and the sensing/ablation electrode 18 is deployed, the distal and proximal coils 48a, 48b of shape-retention or shape-memory wire can be caused to assume a pre-formed shape form the C-shaped configuration of the sensing/ablation electrode 18 to accurately orient the sensing/ablation electrode 18 within the cardiac cavity for the procedure to be performed. As shown in FIGS. 14 and 15, the C-shaped configuration of the sensing/ablation electrode 18 may be used to perform sensing and ablation operations at the ostium of vessels entering the atria.

For example, a shape-memory wire of NiTinol, a nickel-titanium (NiTi) alloy with shape-memory properties may be used to form the distal and proximal coils 48a, 48b. Shape-memory metals, such as NiTinol, are materials that have been plastically deformed to a desired shape before use. Then upon heat application, either from the body as the sheath 6 is inserted into the vasculature or from external sources, the shape-memory material is caused to assume its original shape before being plastically deformed. A shape-memory wire generally exhibits increased tensile strength once the transformation of to the pre-formed shape is completed NiTinol and other shape-memory alloys are able to undergo a "martenistic" phase transformation that enables them to change from a "temporary" shape to a "parent" shape at temperatures above a transition temperature. Below the transition temperature, the alloy can be bent into various shapes. Holding a sample in position in a particular parent shape while heating it to a high temperature programs the alloy to remember the parent shape. Upon cooling, the alloy adopts any temporary shape imparted to it, but when heated again above the transition temperature, the alloy automatically reverts to its parent shape. Alternately, or in addition, shape-memory materials may also be super elastic—able to sustain a large deformation at a constant temperature—and when the deforming force is released they return to their original undeformed shape.

Common formulas of NiTinol have transformation temperatures ranging between −100 and +110° C., have great shape-memory strain, are thermally stable, and have excellent corrosion resistance, which make NiTinol exemplary for use in medical devices for insertion into a patient. For example, the distal and proximal coils 48a, 48b may be designed using NiTinol with a transition temperature around or below room temperature. Before use the catheter 22 and sensing/ablation electrode 18 are stored in a low-temperature state. By flushing the catheter lumen 72 with chilled saline solution, the NiTinol distal and proximal coils 48a, 48b can be kept in the deformed state while positioning the catheter 22 at the desired site. When appropriately positioned, the flow of chilled saline solution can be stopped and the catheter 22 warmed by body heat, or warm saline can be substituted, to allow the NiTinol to recover its "preprogrammed" shape, forming the C-shaped curve of the sensing/ablation electrode 18.

The distal and proximal coils 48a, 48b, extend proximally within their respective coil sleeves 50 within a lumen 72 of the catheter 22. The catheter lumen 72 is depicted to good advantage in FIG. 13. The catheter wall 56 transforms across the transition section 38 into the ablation web 20, the backing web 40, a distal coil wall 56a surrounding the coil sleeve 50 that envelops the distal coil 48a, and a proximal coil wall 56b surrounding the coil sleeve 50 enveloping the proximal coil 48b, as shown to good advantage in FIG. 12. Thus, the catheter wall 56 extends distally to provide a unitary covering for the sensing/ablation electrode 18.

In addition to providing the structure for the distal sensing limb 30a, the distal coil 48a also provides a mounting support for the distal sensors 44a. The even spacing between each loop of the distal coil 48a provides for even spacing of each of the distal sensors 44a. The distal sensors 44a may be hollow metal cylinders or tubes 64, for example, a stainless steel hypo tube, as shown in FIG. 12. Each of the sensor tubes 64 may define a sensor lumen 66 through which a winding of the distal coil 48a passes. Each distal sensor 44a may be affixed to the distal coil 48a at a particular location, for example, by adhering the sensor tube 64 to the winding of the distal coil 48a. In this embodiment, the distal coil 48a is insulated to prevent shorting between the distal sensors 44a, which are individually addressed by specific leads as further described below. In other embodiments however, the distal coil 48a may not be insulated to easily allow for a common signal to travel to each of the distal sensors 44a. Each of the proximal sensors 44b is similarly formed of a sensor tube 64 defining a sensor lumen 66 through which a winding of the proximal coil 48b passes.

As indicated in FIGS. 3B, 4B, and 5B, each of the distal sensors 44a is paired with a corresponding proximal sensor 44b spaced symmetrically along the sensing/ablation electrode 18. It should be recognized that, depending upon the application, the proximal sensors 44b need not be symmetric with the corresponding distal sensors 44a, but instead each of the distal and proximal sensors 44a, 44b may be placed as desired to achieve the desired functionality. As indicated in FIGS. 3B, 4B, and 5B, each of the distal and proximal sensors 44a, 44b is connected with a corresponding sensor lead 52. Each sensor lead 52 is individually addressable to a corresponding distal or proximal sensor 44a, 44b. Each sensor lead 52 only extends distally within the distal or proximal coil 48a, 48b to the extent needed to connect with its corresponding sensor 44a, 44b.

Figure 7:
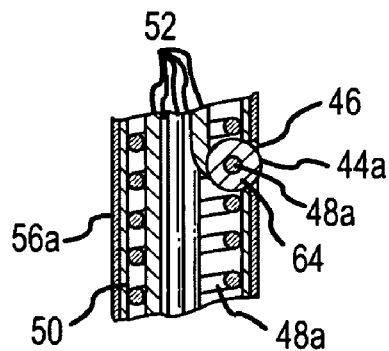
FIG. 7 is a cross-section view of a portion of the sensing/ablation electrode taken along line 7—7 of FIG. 6.
Figure 8:
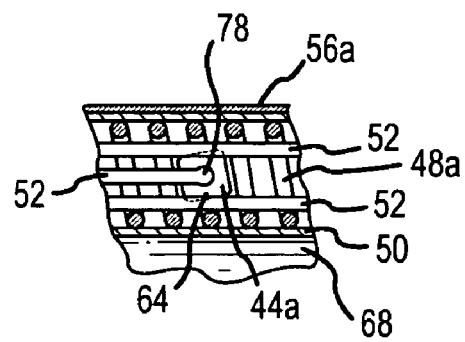
FIG. 8 is a cross-section view of a portion of the sensing/ablation electrode taken along line 8—8 of FIG. 6.

As shown to good advantage in FIGS. 7 and 8, each sensor lead 52 may be connected with a sensor 44a, 44b via wire bond 78 from each corresponding point of connection with the distal and proximal sensors 44a, 44b. Each of the sensor leads 52 travels proximally through the distal and proximal coils 48a, 44b, and through the catheter 22, to ultimately terminate in the handle interface 4 (see FIG. 1). The handle interface 4 may be connected with a sensor diagnostic system (not shown). The sensor diagnostic system in combination with the sensor leads 52 and the sensors 44a, 44b, provides the sensing/ablation catheter 18 with the ability to both evaluate electrocardial transmission paths within cardiac tissue before an ablation procedure is performed as well as to determine the efficacy of an ablation procedure in short-circuiting electrical pathways. For example, the sensor diagnostic system may generate an electrical signal and transmit it through a particular lead to a particular sensor in contact with the patient's cardiac tissue. The path of such electrical signal through the cardiac tissue from the originally energized sensor may be determined by monitoring changes in potential difference between the originally energized sensor and any or all of the remaining sensors.

Although in the embodiment depicted in the figures, both the distal and proximal sensors 44a, 44b are grouped in pairs, and similarly corresponding pairs of distal and proximal sensors 44a, 44b are symmetrically arranged along the sensing/ablation electrode 18, there need not be any electrical coupling between such pairs of sensors either as a result of the arrangement of the sensor leads 52 or by the sensor diagnostic system. In fact any sensor may be coupled with any other sensor for diagnostic purposes, for example, by the use of a patch board within the sensor diagnostic system.

Figure 6:
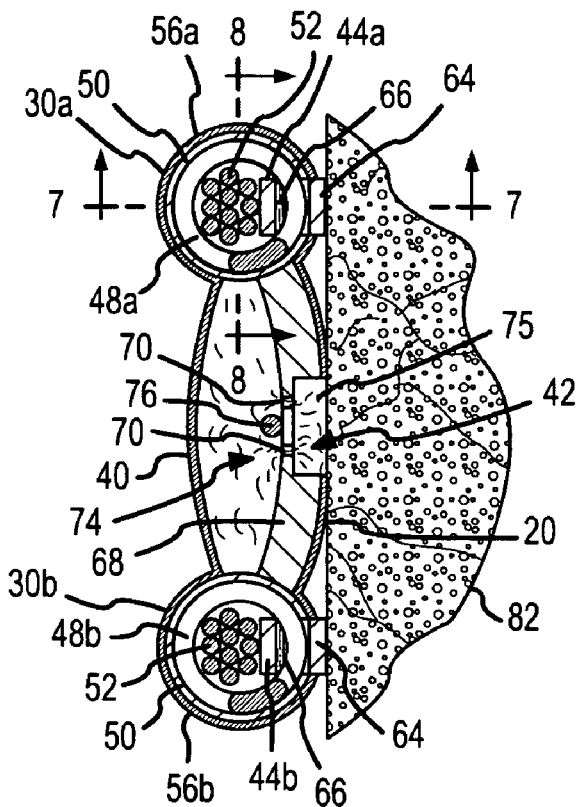
FIG. 6 is a cross-section view of the sensing/ablation electrode taken along line 6—6 of FIG. 5A shown adjacent to a tissue surface.

As shown to good advantage in FIGS. 4B, 5B, and 6B, the ablation membrane 68 extends between the coil sleeve 50 of the distal coil 48a and the coil sleeve 50 of the proximal coil 48b. The edges of the ablation membrane 68 are contiguous with the coil sleeves 50 and may be adhered with the coil sleeves 50 to form a unitary construction. The outward-facing surface of the ablation membrane 68 is adhered to the inward-facing surface of ablation web 20 as shown in FIG. 6. The ablation membrane 68 extends along the length of the sensing/ablation electrode 18 beginning approximately at the inner face between the transition section 38 and the distal end 12 of the sensing/ablation electrode 18. As shown in FIGS. 4B and 5B, a series of aperture pairs are formed within the ablation membrane 68 and function as injection ports 70 to transmit a conductive fluid medium 75 from an electrode lumen 74 defined by the space between the backing web 40 and the ablation membrane 68 to corresponding dispersion ports 42. The backing web 40 and the ablation membrane 68 are sealed together at the distal end of the sensing/ablation electrode 18 in order to prevent leakage of the conductive fluid medium 75 out of the distal end of the electrode lumen 74 and to provide adequate back pressure to force the fluid 75 out of the injection ports 70.

A conductor 77 extends from the proximal end of the catheter 22 between the distal and proximal coils 48a, 48b into the sensing/ablation electrode 18. The conductor 77 may be insulated until it reaches the interface between the transition section 38 and the beginning of the ablation membrane 68. At this point the conductor 77 may extend distally uninsulated to act as an electrode 76 within the sensing/ablation electrode 18. The electrode 76 may be a platinum flat wire for biocompatibility. The electrode 76 may be positioned against the ablation membrane 68 between the pairs of injection ports 70 in order to efficiently energize the fluid 75 as it flows through the injection ports 70 into the dispersion ports 42. The proximal end of the conductor 77 is connected through the handle interface with an appropriate source of ablation energy, for example, a radio frequency energy generator (not shown). This mechanism, wherein energy is transferred from an electrode 76 to the fluid 75, which in turn contacts the tissue 82, without direct contact between the electrode and the tissue 82, is often referred to as a virtual electrode.

The conductive fluid medium 75 flowing through the injection ports 70 and dispersion ports 42 prevents blood from flowing into the sensing/ablation electrode 18 and pushes blood from the area adjacent to the dispersion ports 42. This helps prevent coagulum from forming on the sensing/ablation electrode 18, which can have undesirable effects on the patient. The conductive fluid medium 75 is regulated to flow at a rate that prevents the electrode 76 from overheating the conductive fluid medium 75 and producing vapor in the electrode lumen 74. If the conductive fluid medium 75 were to boil and create a vapor, the ability of the sensing/ablation electrode 18 to form a desired lesion in adjacent tissue 82 would be impaired because of the insufficient transfer of RF energy through the fluid to the tissue 82. Thus, the flow of conductive fluid medium through the electrode lumen 74 and out the injection ports 70 and dispersion ports 42 is managed or regulated so that there is sufficient flow of the fluid 75 to prevent vaporization, but not so much flow that the electrode 76 is unable to sufficiently heat the adjacent tissue 82 to form a desired lesion. Further, if too much conductive fluid medium flows out of the dispersion ports 42, the hemodynamics of the patient may be adversely affected by the excess quantity of fluid 75 mixing with the patient's blood. The desired flow rate is achieved by, for example, adjusting the pressure driving the conductive fluid medium 75 through the electrode lumen 72, changing the diameter or distribution of the dispersion ports 42 and/or the injection ports 70, and altering the spacing between the dispersion ports 42 and/or the injection ports 70.

Another factor that may be taken into account when adjusting the flow rate of the conductive fluid medium 75 is the specific configuration of the distal portion of the sensing/ablation electrode 18 since the flow of conductive fluid medium 75 is affected by the curvature of the catheter 22 and the sensing/ablation electrode 18.

The dispersion ports 42 are formed by the combination of apertures in the ablation web 20 and corresponding recessed areas within the ablation membrane 68. In the embodiments depicted in FIGS. 2, 3A, 4a, and 5A, the dispersion ports 42 are circular in shape, although they may take on any shape depending upon the particular application. In the embodiments depicted, the dispersion ports 42 are evenly spaced along the length of the sensing/ablation electrode 18. As shown in FIGS. 2, 3A, 4A, and 5A, a bridge section 54 of the ablation web 20 extends between each of dispersion ports 42. Even spacing of the dispersion ports 42 may be desirable in order to create a continuous uniform lesion plus a band of tissue. However, depending upon the desired application, wider, narrower, or nonuniform spacing between the dispersion ports 42 may be desirable.

Figure 9:
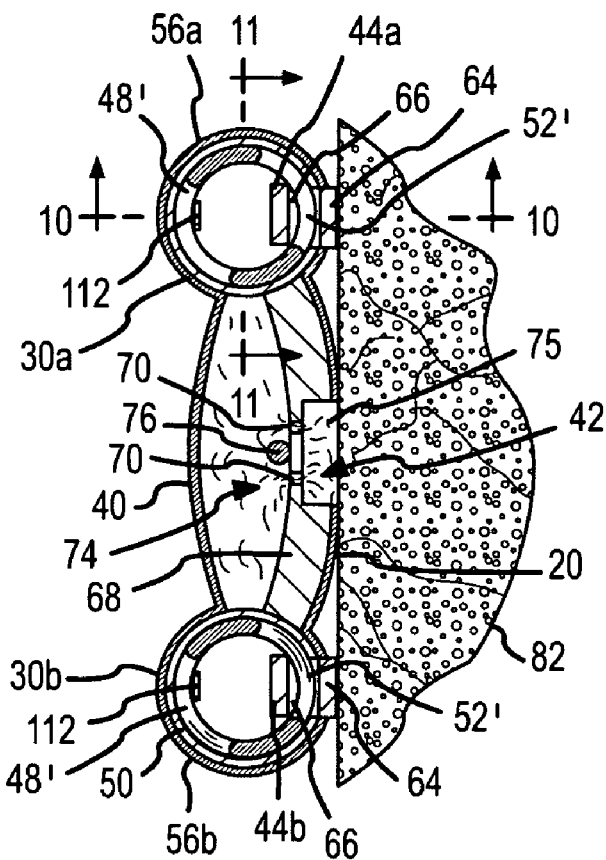
FIG. 9 is a cross-section view of an alternate embodiment of a sensing/ablation electrode, similar to the cross-section of FIG. 6, shown adjacent to a tissue surface.
Figure 10:
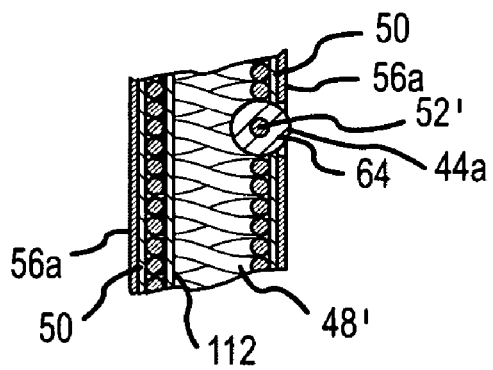
FIG. 10 is a cross-section view of a portion of the sensing/ablation electrode of FIG. 9 taken along line 10—10 of FIG. 9.
Figure 11:
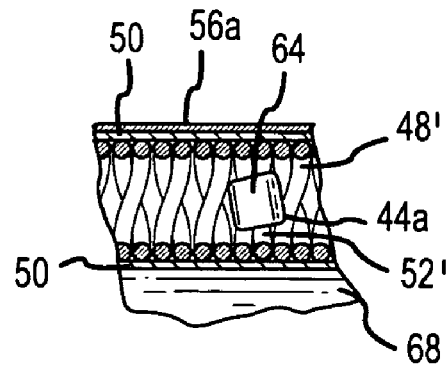
FIG. 11 is a cross-section view of a portion of the sensing/ablation electrode of FIG. 9 taken along line 11—11 of FIG. 9.

FIGS. 9–11 depict an alternative embodiment of the invention. In this embodiment, cylindrical braided limb supports 48' are used to provide the structure for the distal and proximal sensing limbs 30a, 30b instead of the distal and proximal coils. The braided limb supports 48' may be similar to the flat metal cylindrical braid used in forming the catheter wall as described above. In this embodiment the sensor leads 52' may be woven within the metal braid of the braided limb supports 48'. Each sensor lead 52' may be insulated except for a portion that passes through a particular sensor lumen 66 of a particular sensor tube 64 or the distal end which terminates within a particular sensor lumen 66 of a particular sensor tube 64. The uninsulated portion of the sensor lead 52' is electrically coupled with the sensor tube 64.

In order to impart the desired curvature to the sensor/ablation tip of this embodiment, a shape-retention or shape-memory wire 112 may be disposed along an interior wall of each of the braided limb supports 48' as shown in FIGS. 9 and 10. As discussed above, the shape-retention or shape-memory wire, e.g., a flat NiTinol wire, may assume a preformed shape upon deployment of the sensing/ablation tip within the desired cardiac cavity. It should be recognized that a separate shape-memory wire could be incorporated into the previous embodiment of the sensing/ablation catheter to provide the curvature rather than the distal and proximal coils. In such an embodiment, the distal and proximal coils may be of some other composition than a shape memory material and the separate shape-memory wires would impart the curvature to the sensing/ablation catheter.

In an alternative embodiment of the invention, a first limb of the sensing/ablation electrode may be provided with an array of sensors while a second limb of the sensing/ablation electrode may function as a virtual electrode. The second limb in this embodiment defines a fluid-filled lumen and a plurality of apertures including, for example, injection ports and dispersion ports of the previous embodiments. An uninsulated portion of a conductor may be placed within the fluid-filled lumen of the second limb to act as an electrode and energize the fluid exiting the second limb through the apertures. The membrane or web between the first limb and the second limb in this embodiment merely functions as a structural connection between the first limb and second limb to provide a set-off distance between the first and second limbs, to maintain a consistent spacing between the first and second limbs, and to allow the sensing ablation electrode to collapse while within the sheath. Such an embodiment may be desirable in a circumstance where the sensing of signals before or after ablation treatment need only be unidirectional.

The distal ends of the distal and proximal sensing limbs 30a, 30b of the sensing/ablation electrode 18 may be plugged with caps 47 to seal the lumen of the distal and proximal sensing limbs 30a, 30b (see FIGS. 2, 3A, 4A, and 5A). In one embodiment, these caps 47 may function as tip electrodes. If the caps 47 are used as tip electrodes for the sensing/ablation electrode 18, the caps may receive energy from either the same conductor 77 connected to the electrode 76, or a second lead(s) (not shown) may be inserted within the catheter 22 through the distal and proximal sensing limbs 30a, 30b in the sensing/ablation electrode 18 to separately power the tip electrode caps 47. In an alternative embodiment utilizing separate shape-memory wires within the distal and proximal sensing limbs in order to provide the curvature to the sensing/ablation catheter, the shape memory wire may also act as the conductor to transmit energy to caps 48 functioning as tip electrodes.

FIGS. 14–15 schematically depict the sensing/ablation electrode 18 according to the present invention being used to ablate tissue in a left superior pulmonary vein 50. FIGS. 14 and 15 include a number of primary components of the heart to orient the reader. In particular, starting in the upper left-hand portion of FIGS. 14 and 15, and working around the periphery of the heart 80 in a counterclockwise fashion, the following parts of the heart 30 are depicted: the superior vena cava 92, the right atrium 94, the inferior vena cava 96, the right ventricle 98, the left ventricle 100, the left inferior pulmonary vein 102, left superior pulmonary vein 90, the left atrium 104, the right superior pulmonary vein 106, the right inferior pulmonary vein 108, the left pulmonary artery 86, the arch of the aorta 84, and the right pulmonary artery 88.

The distal end of the sensing/ablation electrode 18 is positioned adjacent to the ostium 110 of the left superior pulmonary vein 90 using known procedures. For example, to place the sensing/ablation electrode 18 in the position shown in FIG. 11, the right venous system may be first accessed using the "Seldinger technique." In this technique, a peripheral vein (such as a femoral vein) is first punctured with a needle and the puncture wound is dilated with a dilator to a size sufficient to accommodate an introducer (e.g., the outer guiding introducer 26). The outer guiding introducer 26 with at least one hemostatic valve (see FIG. 1) is seated within the dilated puncture wound while maintaining relative hemostasis. From there, the outer guiding introducer 26 is advanced along the peripheral vein, into the inferior vena cava 96, and into the right atrium 94. A transeptal sheath may be further advanced through the outer guiding introducer 26 to create a hole in the interatrial septum between the right atrium 94 and the left atrium 104. Once the outer guiding introducer 26 is in place in the right atrium 94, the inner guiding introducer 28, housing the catheter 22 with the sensing/ablation electrode 18 on the distal end, is introduced through the hemostatic valve of the outer guiding introducer 26 and navigated into the right atrium 94, through the hole in the interatrial septum, and into the left atrium 104. Once the inner guiding introducer 28 is in the left atrium 104, the catheter 22 and attached sensing/ablation electrode 18 may be advanced through distal tip 58 of the inner guiding introducer 28 to the positions depicted in FIGS. 14 and 15.

In FIG. 15, the sensing/ablation electrode 18 is shown inserted into the ostium 110 left superior pulmonary vein 90 in contact with the tissue of the walls of the vein. The configuration of the sensing/ablation electrode 18 as depicted in FIG. 2 is advantageous for maintaining consistent contact with tissue in a generally cylindrical vessel. However, some vessels may not be cylindrical, especially at the ostium of a vessel as it enters a cardiac cavity and generally flares outward to a greater diameter. In such instances, it may be difficult to achieve consistent contact between the sensing/ablation electrode and the tissue over the entire length of the sensing/ablation electrode. In some embodiments, therefore, the length of the proximal sensing limb 30a may be longer or shorter than the length of the distal sensing limb 30b. The proximal and distal sensing limbs may be positioned such that they are centered with respect to each other. In this manner, a trapezoidal-shaped sensing and ablation electrode may be formed to better fit the flared shape of the ostium of certain vessels or other imperfect vessel shapes.

While the sensing/ablation electrode 18 is in the left superior pulmonary vein 90 as shown in FIG. 15, the electrode may be activated to create the desired lesion in the left superior pulmonary vein 90. As shown in FIGS. 6 and 9, the RF energy emanating from the electrode 76 is transmitted through the conductive fluid medium 75 in the electrode lumen 74, through the injection ports 70, into the dispersion ports 42, and into the adjacent tissue 82. Thus, a lesion is formed in the tissue 82 by the RF energy. The conductive fluid medium 75 may also experience ohmic heating as it flows along the electrode 76 and out the injection ports 70 and dispersion ports 42. Lesion formation may thus also be facilitated by the conductive fluid medium 75, which may have been heated by ohmic heating to a sufficiently high temperature to facilitate or enhance lesion formation. The RF energy is conducted into the adjacent tissue 82 and the heated conductive fluid medium 75 convectively affects the temperature of the tissue 82. In order to form a sufficient lesion, it is desirable to raise the temperature of the tissue 82 to at least 50° C. for an appropriate length of time (e.g., one minute). Thus, sufficient RF energy must be supplied to the electrode 76 to produce this lesion-forming temperature in the adjacent tissue 82 for the desired duration.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A cardiac sensing and ablation device for intravascular insertion in a patient, the cardiac sensing and ablation device comprising
   a bifurcated sensing portion further comprising
      a first sensing limb;
      a first set of a plurality of sensors disposed upon the first sensing limb;
      a second sensing limb, parallel with but spaced apart from the first sensing limb; and
      a second set of a plurality of sensors disposed upon the second sensing limb; and
   an ablation web disposed between the first sensing limb and the second sensing limb, the ablation web further comprising an electrode, wherein
   the first set of sensors, the second set of sensors, and the electrode lie substantially within the same curvilinear plane.

2. The cardiac sensing and ablation device of claim 1, wherein
   the bifurcated sensing portion and the ablation web assume a pre-shaped curved form;
   the first set of sensors is positioned on a surface of the first sensing limb defining an outer surface of the curved form; and
   the second set of sensors is positioned on a surface of the second sensing limb defining the outer surface of the curved form.

3. The cardiac sensing and ablation device of claim 1, wherein the ablation web further comprises a pliable web disposed to bend longitudinally parallel to the first sensing limb and the second sensing limb providing variable spacing between the first sensing limb and the second sensing limb.

4. The cardiac sensing and ablation device of claim 1 further comprising a plurality of lead wires, wherein each lead wire is coupled with a respective one of the first set of sensors or a respective one of the second set of sensors.

5. The cardiac sensing and ablation device of claim 1, wherein each of the first sensing limb and the second sensing limb comprise a support structure covered by a respective sleeve.

6. The cardiac sensing and ablation device of claim 5, wherein the support structure comprises at least one conductor coupled with at least one of the first set of sensors or one of the second set of sensors.

7. A cardiac sensing and ablation system comprising
   a catheter; and
   a sensing array and ablation electrode disposed on a distal end of the catheter, the sensing and ablation electrode further comprising
      a first sensing limb;
      a first set of a plurality of sensors disposed upon the first sensing limb;
      a second sensing limb, parallel with but spaced apart from the first sensing limb; and
      a second set of a plurality of sensors disposed upon the second sensing limb;
      a first membrane disposed between the first sensing limb and the second sensing limb, wherein
      the first membrane defines a plurality of apertures adapted to disperse a fluid; and
      the first set of sensors, the second set of sensors, and the plurality of apertures lie substantially within the same curvilinear plane;

a second membrane disposed between the first sensing limb and the second sensing limb, wherein an electrode lumen is defined between the first membrane, the second membrane, the first sensing limb, and the second sensing limb; and an electrode conductor positioned between the first membrane and the second membrane adjacent the plurality of apertures.

8. The cardiac sensing and ablation system of claim 7 further comprising
a shape retention wire positioned within the sensing array and ablation electrode that assumes a curved form when not otherwise restrained and causes the sensing array and ablation electrode to assume a ribbon-like form following the curved form.

9. The cardiac sensing and ablation system of claim 8, wherein
the first sensing limb is symmetric to and instantaneously parallel to the second sensing limb;
the first set of sensors is positioned on a surface of the first sensing limb, the position of each of the sensors in the first set defining an outer surface of the ribbon-like form;
the second set of sensors is positioned on a surface of the second sensing limb, the position of each of the sensors in the second set defining the outer surface of the ribbon-like form; and
each of the apertures in the first membrane is immediately adjacent to a respective line tangential to both the surface of the first sensing limb defining the outer surface of the ribbon-like form and the surface of the second sensing limb defining the outer surface of the ribbon-like form.

10. The cardiac sensing and ablation system of claim 8, wherein the shape retention wire comprises a shape memory material.

11. The cardiac sensing and ablation system of claim 7, wherein
the first sensing limb further comprises a first coil covered by a first sleeve; and
the second sensing limb further comprises a second coil covered by a second sleeve.

12. The cardiac sensing and ablation system of claim 11, wherein each of the sensors in the first set is positioned on a respective winding of the coil.

13. The cardiac sensing and ablation system of claim 11, further comprising
a first set of a plurality of lead wires positioned within the first coil, wherein each lead wire of the first set is coupled with a respective one of the first set of sensors; and
a second set of a plurality of lead wires positioned within the second coil, wherein each lead wire of the second set is coupled with or a respective one of the second set of sensors.

14. The cardiac sensing and ablation system of claim 11, wherein at least one of the first coil and the second coil is further a shape retention wire and assumes a curved form when not otherwise restrained and causes the sensing array and ablation electrode to assume a ribbon-like form following the curved form.

15. The cardiac sensing and ablation system of claim 14, wherein
the first sensing limb is symmetric to and instantaneously parallel to the second sensing limb;
the first set of sensors is positioned on a surface of the first sensing limb, the position of each of the sensors in the first set defining an outer surface of the ribbon-like form;

the second set of sensors is positioned on a surface of the second sensing limb, the position of each of the sensors in the second set defining the outer surface of the ribbon-like form; and
each of the apertures in the first membrane is immediately adjacent to a respective line tangential to both the surface of the first sensing limb defining the outer surface of the ribbon-like form and the surface of the second sensing limb defining the outer surface of the ribbon-like form.

16. The cardiac sensing and ablation system of claim 7, wherein
the first sensing limb further comprises a first braided wire tube covered by a first sleeve; and
the second sensing limb further comprises a second braided wire tube covered by a second sleeve.

17. The cardiac sensing and ablation system of claim 16, further comprising
a first set of a plurality of lead wires woven within the first braided wire tube, wherein each lead wire of the first set is coupled with a respective one of the first set of sensors; and
a second set of a plurality of lead wires woven within the second braided wire tube, wherein each lead wire of the second set is coupled with or a respective one of the second set of sensors.

18. The cardiac sensing and ablation system of claim 7, further comprising
a sheath surrounding the catheter, the sheath defining a lumen of a certain cross-sectional area at a distal tip of the sheath, wherein
when the sensing array and ablation electrode is not housed within the sheath, a distance between a first outer surface of the first sensing limb and a second outer surface of the second sensing limb is greater than a greatest diameter of the certain cross-sectional area.

19. The cardiac sensing and ablation system of claim 7, wherein the first membrane further comprises a first pliable web and the second membrane further comprises a second pliable web, wherein each of the first membrane and the second membrane is disposed to bend longitudinally parallel to the first sensing limb and the second sensing limb providing variable spacing between the first sensing limb and the second sensing limb.

20. The cardiac sensing and ablation system of claim 19, wherein
the first membrane is disposed to bend to form a first convex surface in a first direction;
the second membrane is disposed to bend to form a second convex surface in a second direction; and
the first direction is opposite the second direction.

21. The cardiac sensing and ablation system of claim 7, wherein the plurality of apertures comprises an array of pairs of apertures and the electrode conductor is positioned between each pair of apertures.

22. The cardiac sensing and ablation system of claim 21, wherein each pair of apertures fluidly connects the electrode lumen to a respective dispersion port formed as a recess in an outer wall of the first membrane.

23. The cardiac sensing and ablation system of claim 22, wherein a diameter of each dispersion port is greater than a separation distance between a respective pair of apertures.

24. A bifurcated, collapsible electrode for intravascular insertion in a patient, the electrode comprising
a first limb;
a plurality of sensors disposed upon the first limb;
a second limb, parallel with but spaced apart from the first limb;
an electrode supported by the second sensing limb; and a flexible membrane connected with and disposed between the first limb and the second limb, wherein the plurality of sensors and the electrode lie substantially within the same curvilinear plane.

25. The bifurcated, collapsible electrode of claim 24, wherein the first limb and the second limb assume a curved form;

the plurality of sensors is positioned on a surface of the first limb and defines an outer surface of the curved form; and a tissue contacting portion of the electrode is positioned on a surface of the second limb defining the outer surface of the curved form.

26. The bifurcated, collapsible electrode of claim 24, wherein the flexible membrane is disposed to bend longitudinally parallel to the first limb and the second limb providing variable spacing between the first limb and the second limb.

27. The bifurcated, collapsible electrode of claim 24, wherein the second limb comprises an outer wall defining a lumen for transporting a conductive fluid medium;

the outer wall defines at least one aperture fluidally connected with the lumen; and an electrode wire is disposed within the lumen of the second limb.

* * * * *